United States Patent
Mansour et al.

(10) Patent No.: US 12,364,849 B2
(45) Date of Patent: Jul. 22, 2025

(54) MALE LUER WITH FLUID PATH AND VENT PATH SEALS

(71) Applicant: CareFusion 303, Inc., San Diego, CA (US)

(72) Inventors: George Michel Mansour, Diamond Bar, CA (US); Tyler Devin Panian, Long Beach, CA (US)

(73) Assignee: CareFusion 303, Inc., San Diego, CA (US)

( * ) Notice: Subject to any disclaimer, the term of this patent is extended or adjusted under 35 U.S.C. 154(b) by 897 days.

(21) Appl. No.: 17/520,397

(22) Filed: Nov. 5, 2021

(65) Prior Publication Data

US 2022/0054818 A1    Feb. 24, 2022

Related U.S. Application Data

(63) Continuation of application No. 16/383,418, filed on Apr. 12, 2019, now Pat. No. 11,213,668, which is a
(Continued)

(51) Int. Cl.
| | |
|---|---|
| *A61M 39/26* | (2006.01) |
| *A61M 39/10* | (2006.01) |
| *A61M 39/22* | (2006.01) |

(52) U.S. Cl.
CPC ............ *A61M 39/26* (2013.01); *A61M 39/10* (2013.01); *A61M 39/22* (2013.01); *A61M 2039/266* (2013.01); *A61M 2039/268* (2013.01)

(58) Field of Classification Search
CPC ...... A61M 39/26; A61M 39/10; A61M 39/22; A61M 39/06; A61M 39/0613;
(Continued)

(56) References Cited

U.S. PATENT DOCUMENTS

| | | | |
|---|---|---|---|
| 5,269,771 A | 12/1993 | Thomas et al. | |
| 6,039,302 A | * 3/2000 | Cote, Sr. | ........... A61M 39/26 604/905 |

(Continued)

FOREIGN PATENT DOCUMENTS

| | | |
|---|---|---|
| CN | 101111282 A | 1/2008 |
| CN | 101152594 A | 4/2008 |

(Continued)

OTHER PUBLICATIONS

Australian Examination Report No. 1 for Application No. 2014249908, Nov. 8, 2017, 6 pages.

(Continued)

*Primary Examiner* — Kevin C Sirmons
*Assistant Examiner* — Alexandra Lalonde

(57) ABSTRACT

A needleless connector includes a body having a fluid path, a vent path, and a male fitting. The needleless connector also includes a valve disposed within the male fitting. The valve is configured to move between a first configuration, in which the fluid path is blocked, and a second configuration, in which the fluid path is open. The needleless connector further includes a seal disposed around the valve. The seal is configured to separate the fluid path from the vent path in the first configuration and the second configuration. Moving the valve from the first configuration to the second configuration also opens the vent path. The seal maintains the separation between the fluid path and the vent path when the valve moves from the first configuration to the second configuration.

19 Claims, 3 Drawing Sheets

Related U.S. Application Data continuation of application No. 15/097,224, filed on Apr. 12, 2016, now Pat. No. 10,300,265, which is a continuation of application No. 13/797,688, filed on Mar. 12, 2013, now Pat. No. 9,308,362.

(58) Field of Classification Search
CPC .............. A61M 39/0693; A61M 39/24; A61M 2039/266; A61M 2039/268; A61M 2039/062; A61M 2039/0626; A61M 2039/0633; A61M 2039/064; A61M 2039/0673; A61M 2039/0686; A61M 2039/242; A61M 2039/2426; A61M 2039/2433; A61M 2039/2486; A61M 2039/263; A61M 2039/267
See application file for complete search history.

(56) References Cited

U.S. PATENT DOCUMENTS

| | | | |
|---|---|---|---|
| 2003/0032940 A1* | 2/2003 | Doyle | A61M 39/045 604/533 |
| 2004/0124388 A1 | 7/2004 | Kiehne | |
| 2004/0172006 A1 | 9/2004 | Bonaldo | |
| 2006/0192164 A1 | 8/2006 | Korogi | |
| 2009/0198211 A1 | 8/2009 | Thorne, Jr. et al. | |
| 2010/0174242 A1 | 7/2010 | Anderson et al. | |
| 2010/0256573 A1 | 10/2010 | Mansour et al. | |
| 2011/0130724 A1 | 6/2011 | Mansour et al. | |

FOREIGN PATENT DOCUMENTS

| | | |
|---|---|---|
| CN | 201533946 U | 7/2010 |
| CN | 102019032 A | 4/2011 |
| CN | 102458505 A | 5/2012 |
| CN | 102573953 A | 7/2012 |
| CN | 102316925 A | 4/2017 |
| EP | 2269687 A2 | 1/2011 |
| JP | 2001505102 A | 4/2001 |
| JP | 2001506156 A | 5/2001 |
| JP | 2008522729 A | 7/2008 |
| JP | 2008522736 A | 7/2008 |
| JP | 2008264030 A | 11/2008 |
| JP | 2012512726 A | 6/2012 |
| JP | 2012522577 A | 9/2012 |
| JP | 2016510656 | 4/2016 |
| WO | WO-2003013646 A2 | 2/2003 |
| WO | WO-2003018105 A1 | 3/2003 |
| WO | WO-2006062912 | 6/2006 |
| WO | WO-2006078355 | 7/2006 |
| WO | WO-2006088858 A2 | 8/2006 |
| WO | WO-2007073939 A1 | 7/2007 |
| WO | WO-2009117135 | 9/2009 |
| WO | WO-2010071848 A1 | 6/2010 |
| WO | WO-2011060384 A1 | 5/2011 |
| WO | WO-2011119347 A2 | 9/2011 |
| WO | WO-2013002320 A1 | 1/2013 |

OTHER PUBLICATIONS

Australian Office Action for Application No. 2019200750, dated Aug. 7, 2019, 5 pages.
Australian Office Action for Application No. 2020250200, dated Jun. 30, 2021, 3 pages.
Canadian Office Action for Application No. 2900999, dated Nov. 29, 2019, 4 pages.
Chinese Office Action for Application No. 201480014558.3, dated Feb. 4, 2017, 10 pages excluding English translation.
Chinese Office Action for Application No. 201711283412.0, dated Dec. 30, 2019, 9 pages.
European Office Action for Application No. 18204668.0, dated Feb. 11, 2021, 5 pages.
Extended European Search Report for Application No. 182046680, dated Jan. 15, 2019, 9 pages.
Japanese Office Action for Application No. 2016500366, dated Nov. 28, 2017, 4 pages excluding English translation.
Japanese Office Action for Application No. 2018074009, dated Jan. 29, 2019, 11 pages.
Japanese Office Action for Application No. 2018-074009, dated Jun. 18, 2019, 8 pages.
Japanese Office Action for Application No. 2019188383, dated Jun. 22, 2021, 4 pages including translation.
Japanese Office Action for Application No. 2019-1888383, dated Oct. 23, 2020, 9 pages including translation.
Japanese Office Action for Application No. 2021-170691 dated Jan. 6, 2023, 4 pages including translation.
Australian Office Action for Application No. 2022200461, dated Jul. 6, 2023, 5 pages.

* cited by examiner

PROXIMAL ⟵⟶ DISTAL
*PRIOR ART*

MALE LUER WITH FLUID PATH AND VENT PATH SEALS

CROSS-REFERENCES TO RELATED APPLICATIONS

This application is a continuation of U.S. patent application Ser. No. 16/383,418, entitled "MALE LUER WITH FLUID PATH AND VENT PATH SEALS," filed Apr. 12, 2019, which issued on Jan. 4, 2022, as U.S. Pat. No. 11,213,668, which is a continuation of U.S. patent application Ser. No. 15/097,224, entitled "MALE LUER WITH FLUID PATH AND VENT PATH SEALS," filed Apr. 12, 2016, which issued on May 28, 2019, as U.S. Pat. No. 10,300,265, which is a continuation of U.S. patent application Ser. No. 13/797,688, entitled 'MALE LUER WITH FLUID PATH AND VENT PATH SEALS," filed Mar. 12, 2013, which issued on Apr. 12, 2016, as U.S. Pat. No. 9,308,362. The entire content of these applications is incorporated by referenced herein.

BACKGROUND

Field

The present disclosure generally relates to needleless connectors, and, in particular, to self-sealing male needleless connectors.

Description of the Related Art

Medical treatments often include the infusion of a medical fluid, for example a saline solution or a liquid medication, to patients using an intravenous (IV) catheter that is connected though an arrangement of flexible tubing and fittings, commonly referred to as an "IV set," to a source of fluid, for example an IV bag. Needleless fittings commonly include male and female needleless connectors having a "Luer taper" conforming to an International Standards Organization (ISO) standard wherein mating of Luer fittings forms a liquid-tight connection.

Certain connectors have a self-sealing feature to prevent leakage of fluid from the attached tubing when the connector is decoupled from a mating connector. Typical self-sealing needleless connectors provide only a fluid path and, therefore, provide a self-sealing capability only for the fluid path.

SUMMARY

The needleless male connector disclosed herein provides both a fluid path and a vent path, each having a self-sealing feature wherein connection of the disclosed male connector to a compatible female connector opens both the fluid and vent paths and disconnection closes both paths.

In certain embodiments, a needleless connector includes a body having a male fitting, a valve disposed within the body, the body and the valve defining a vent path and a fluid path, a sealing tip disposed over a portion of the valve, and a sliding seal disposed over a portion of the male fitting. The sealing tip and the sliding seal are configured to one of open the vent path before opening the fluid path as the valve moves from a first valve position to a second valve position, and open the fluid path before opening the vent path as the valve moves from the first valve position to the second valve position.

In certain embodiments, a needleless connector set includes a male connector having a first body having a male fitting, a valve disposed within the first body, the first body and the valve defining a vent path and a fluid path, a sealing tip disposed over a portion of the valve, and a sliding seal disposed over a portion of the male fitting. The sealing tip and the sliding seal are configured to one of open the vent path before opening the fluid path as the valve moves from a first valve position to a second valve position and open the fluid path before opening the vent path as the valve moves from the first valve position to the second valve position. The needleless connector set also includes a female connector including a second body and a collapsible valve disposed within the second body, wherein the valve is in the first valve position when the male connector and the female connector are not mated and in the second valve position when the male connector and the female connector are mated.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The needleless male connector disclosed herein provides both a fluid path and a vent path, each having a self-sealing feature wherein connection of the disclosed male connector to a compatible female connector opens both the fluid and vent paths and disconnection closes both paths.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

Figure 1A:
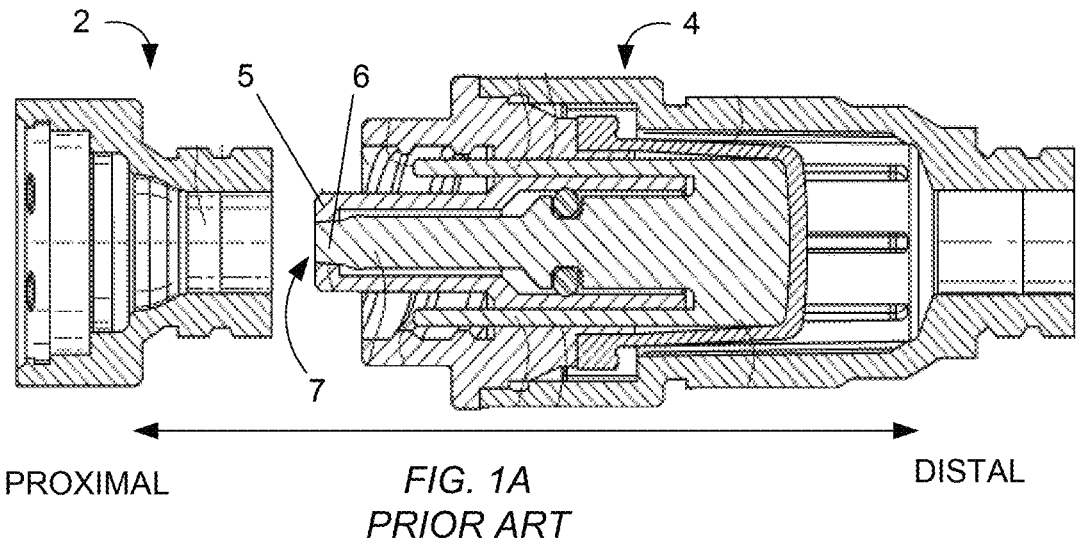
FIGS. 1A-1C are cross-sections of a conventional needleless male connector.
Figure 1B:
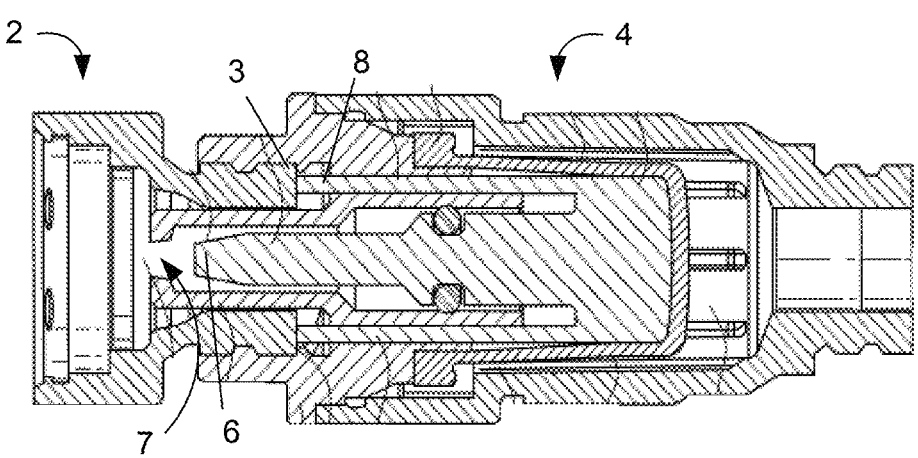
Figure 1C:
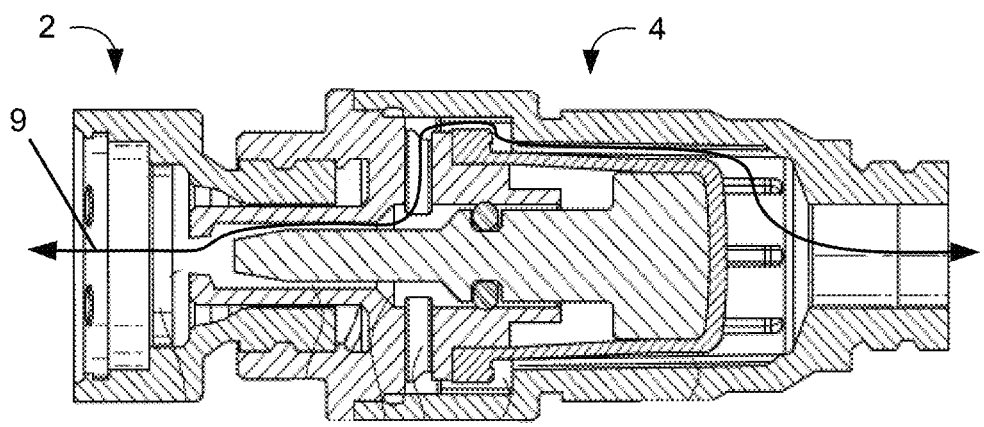

FIGS. 1A-1C are cross-sections of a conventional needleless male connector 4 as disclosed in U.S. Pat. No. 8,182,452. FIG. 1A depicts the male connector 4 and a compatible female connector 2 prior to being mated. The connector 4 has a male fitting 5 with a port 7 on the tip. An internal valve 6 slides relative to the fitting 5 and is biased toward the proximal direction such that the tip of the valve 6 seals the port 7 when the male connector 4 is not mated with female connector 2.

FIGS. 1B and 1C are cross-sections taken on perpendicular planes through the mated connectors 2 and 4. In this configuration, the face 3 of the female connector 2 has contacted posts 8 that are connected to the valve 6 and displaced the posts 8, and therefore the valve 6, in a distal direction. This motion displaces the tip of valve 6 from the port 7, thereby allowing fluid to flow through the mated connectors 2 and 4 along the flow path 9.

It can be seen from the FIGS. 1A-1C that there is no gas flow path through the connectors 2 and 4, nor is there a closable vent path to the ambient atmosphere of any gas-filled portion of the male connector 4. This is typical of conventional fluid needleless connectors in that they are generally intended for connecting fluid lines, for example the fluid lines of a medical intravenous (IV) set.

Figure 2A:
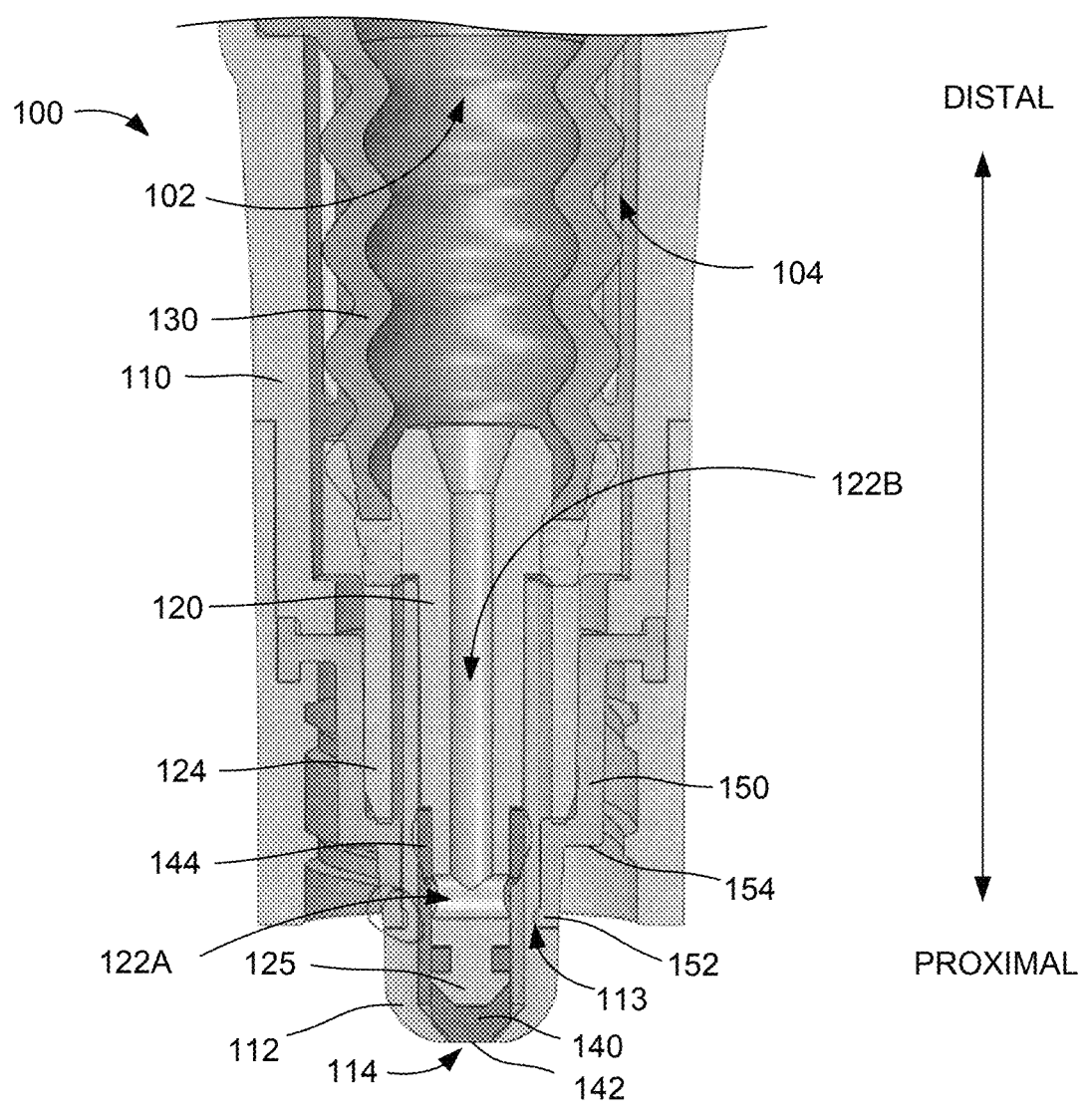
FIGS. 2A-2B are cross-sections of an exemplary male needleless connector and a compatible female connector according to certain aspects of the present disclosure.
Figure 2B:
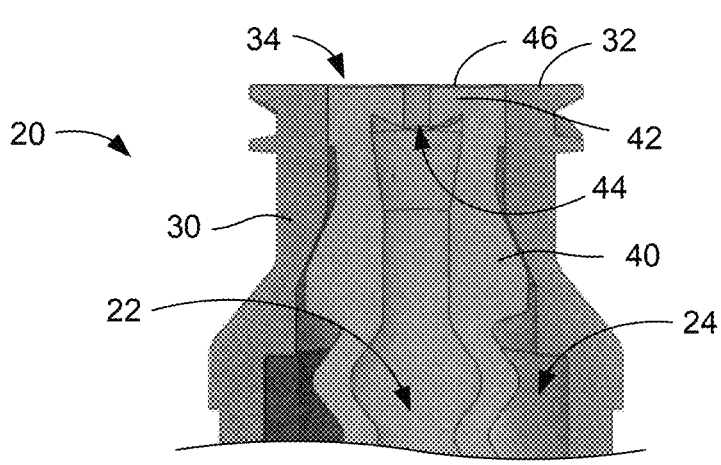

FIGS. 2A-2B are cross-sections of an exemplary male needleless connector 100 and a compatible female connector 20 according to certain aspects of the present disclosure. The male needleless connector 100 shown in FIG. 2A has a body 110 with a male Luer fitting 112 with a port 114 at a proximal end of the fitting 112. In certain embodiments, the male fitting 112 does not have a Luer taper. A valve 120 is slidably disposed within the body 110 and partially within the male fitting 112. A sealing tip 140 is disposed over a proximal tip 124 of the valve 120. The valve 120 is biased in the proximal direction by the action of an accordion bellows 130 disposed within cavity 104 distal to the valve 120 such that the sealing tip 140 sealingly contacts the port 114 of the male fitting 112. In this configuration, the external surface 142 of the sealing tip 140 is approximately flush with the external surface of the male fitting 112 around the port 114. The sealing tip 140 includes a second seal 144 that forms a sliding seal between the valve 120 and the male fitting 112.

A passage 122 passes through the valve 120 and the sealing tip 140 and comprises, in this example, a longitudinal fluid passage 122B that passes from the open internal cavity 102 of the bellows 130 to a lateral fluid passage 122A that is open to the interior of the male fitting 112. The internal cavity 102 connects to a fluid passage of an attached fluid line or fitting (not shown in FIG. 2A).

FIGS. 2A-2B are cross-sections of an exemplary male needleless connector 100 and a compatible female connector 20 according to certain aspects of the present disclosure. The male needleless connector 100 shown in FIG. 2A has a body 110 with a male Luer fitting 112 with a port 114 at a proximal end of the fitting 112. In certain embodiments, the male fitting 112 does not have a Luer taper. A valve 120 is slidably disposed within the body 110 and partially within the male fitting 112. A sealing tip 140 is disposed over a proximal tip 125 of the valve 120. The valve 120 is biased in the proximal direction by the action of an accordion bellows 130 disposed within cavity 104 distal to the valve 120 such that the sealing tip 140 sealingly contacts the port 114 of the male fitting 112. In this configuration, the external surface 142 of the sealing tip 140 is approximately flush with the external surface of the male fitting 112 around the port 114. The sealing tip 140 includes a second seal 144 that forms a sliding seal between the valve 120 and the male fitting 112.

A sliding seal 150 is disposed over a portion of the male fitting 112 and the fingers 124 with a tip 152 of the sliding seal 150 in sealing contact with a recess 113 in the male fitting 112. A distal end of the sliding seal 150 is captured, in this example, between two components that form the body 110. The sliding seal 150 also has a shoulder 154 disposed proximate to the proximal tips of the fingers 124. In certain embodiments, the sliding seal comprises an elastomeric material. In certain embodiments, the sliding seal comprises a flexible material.

FIG. 2B illustrates certain features of a compatible female fitting 20 that, in this example, is a female Luer fitting that is compatible with the example male Luer fitting of FIG. 2A. In certain embodiments, the connector 20 does not have a Luer taper. The connector 20 has a body 30 with a distal surface 32 and an opening 34. A collapsible valve 40 is disposed within the body 30 and has a distal end 42 that, in this configuration, is disposed within the opening 34 such that the distal face 46 is approximately flush with the distal surface 32 of the body 30. The tip 42 comprises a slit 44 that is forced closed when the tip 42 is positioned as shown in FIG. 2B and will self-open when the collapsible valve 40 is displaced in a proximal direction such that the tip 42 is displaced into the wider cavity 24 of the body 30. The slit 44 passes from the distal face 46 into the internal passage 22 that connects to a fluid passage of an attached fluid line or fitting (not shown in FIG. 2B).

Figure 3:
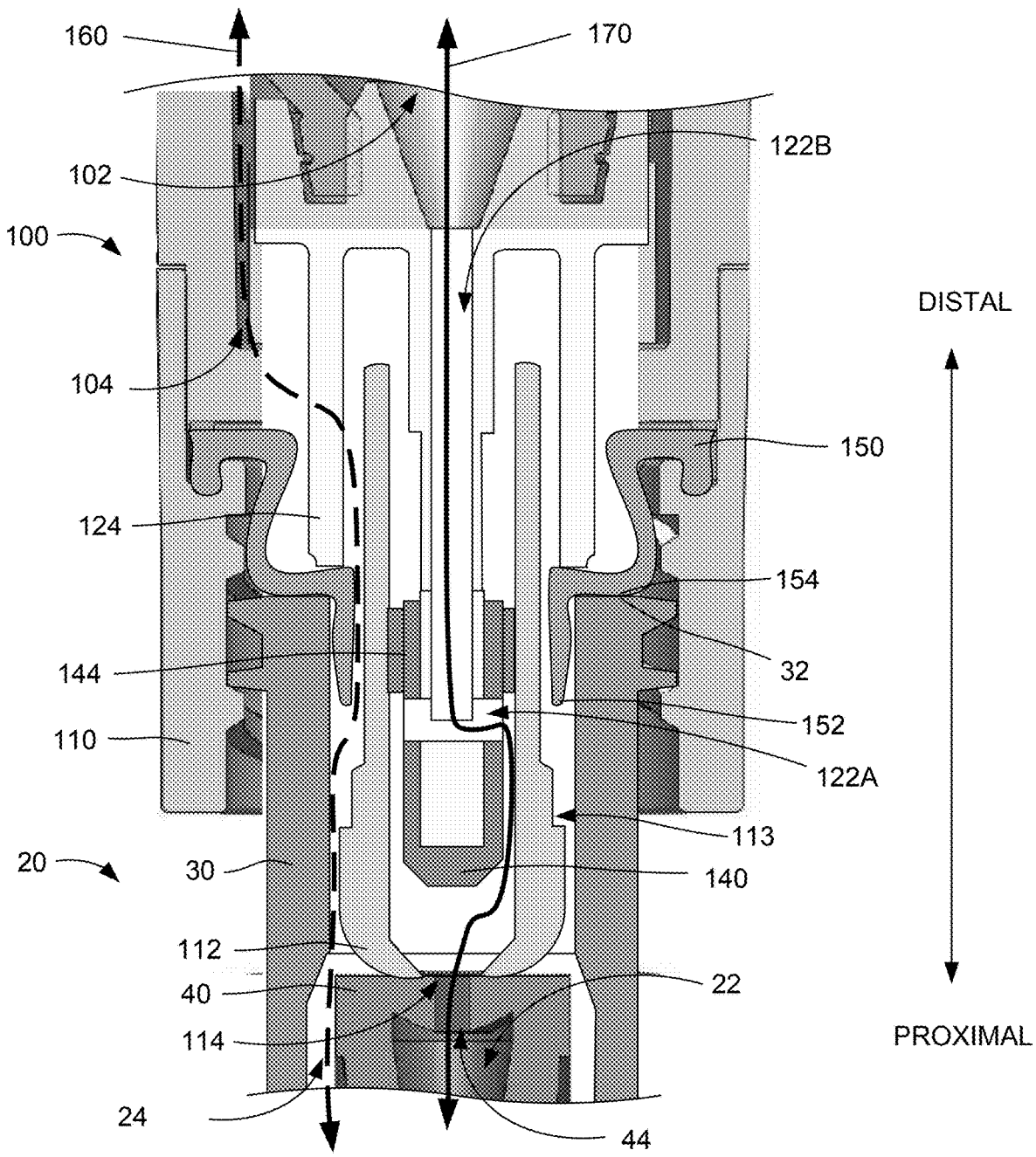
FIG. 3 is a cross-section depicting the male and female connectors of FIGS. 2A-2B in an engaged configuration according to certain aspects of the present disclosure.

FIG. 3 is a cross-section depicting the male and female connectors 100, 20 of FIGS. 2A-2B in an engaged configuration according to certain aspects of the present disclosure. The body 30 of the female connector 20 has been threaded into the body 110 of the male fitting 112 such that the connectors 100, 20 are retained in the engaged configuration. As the body 30 was threaded into the body 110, the distal surface 32 of the body 30 came into contact with the shoulder 154 of the sliding seal 150 and, as the body 30 advanced into the body 110, displaced the shoulder 154 and the adjacent fingers 124 in a distal direction. As the distal end of the sliding seal 150 is captured by the body 110, the displacement of the shoulder 154 collapses the sliding seal 150 generally as shown, as an example, in FIG. 3. The displacement of the shoulder 154 also draws the tip 152 of the sliding seal 150 away from the recess 113, thereby opening a vent path 160 from the cavity 104 between the sliding seal 150 and the male fitting 114 into the internal cavity 24, indicated in FIG. 3 by the dashed line labeled "160."

The distal displacement of the finger 124 causes the entire valve 120 to move in the distal direction, thereby distally displacing the second seal 144 within the male fitting 112 and the sealing tip 140 from the port 114. At the same time, the male fitting 112 displaced the collapsible valve 40 such that the slit 44 self-opened. As the second seal 144 maintains the seal between the valve 120 and male fitting 112, a fluid path 170 is now provided from the internal cavity 102 through the mated connectors 100, 20 to the internal passage 22, as indicated by the solid line labeled "170." It can be seen that the fluid path 170 and the vent path 160 are separated by seals between the male fitting 112 and the collapsible valve 40, between the second seal 144 of the sealing tip 140 and the male fitting 112, and between the accordion bellows 130 and the valve 120. In certain embodiments, the vent path 160 may open before the fluid path 170. In other embodiments, the fluid path 170 may open before the vent path 160. In other embodiments, the fluid path 170 and the vent path 160 may open at approximately the same time.

In certain embodiments, the sliding seal 150 may form a sealing contact with the male fitting 112 in locations other than tip 152. In certain embodiments, the recess 113 may be absent and the tip 152 seals against a smooth external surface of the male fitting 112. In certain embodiments, the male fitting 112 may have external features (not shown), for example ridges running in a distal-proximal direction, that expand, as the sliding seal is displaced, a portion of the sliding seal 150 that sealingly contacts the fitting 112 when in an undisplaced configuration.

In summary, it can be seen that the disclosed embodiments of the needleless connector provide a fluid path and a vent path that are each sealed when the male and female connectors are not mated and are opened automatically as the connectors are mated.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The term "exemplary" is used herein to mean "serving as an example or illustration." Any aspect or design described herein as "exemplary" is not necessarily to be construed as preferred or advantageous over other aspects or designs.

The terms "include," "have," "with," and the like are intended to be inclusive in a manner similar to the term "comprise" as "comprise" is interpreted when employed as a transitional word in a claim.

No claim element is to be construed under the provisions of 35 U.S.C. § 112, sixth paragraph, unless the element is expressly recited using the phrase "means for" or, in the case of a method claim, the element is recited using the phrase "step for."

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A needleless connector comprising:
a body having a proximal end with a male fitting and an opposing distal end;
a valve disposed within the body, the body and the valve defining a vent path between the distal end and the proximal end and a fluid path between the distal end and the proximal end, each of the vent path and the fluid path extending from a most proximal surface of the proximal end to a most distal surface of the distal end;
a sealing tip disposed over a portion of the valve; and
a sliding seal disposed over a portion of the male fitting, wherein the sealing tip and the sliding seal are configured to one of:
open the vent path before opening the fluid path as the valve moves from a first valve position to a second valve position; and
open the fluid path before opening the vent path as the valve moves from the first valve position to the second valve position.

2. The needleless connector of claim 1, wherein the sealing tip comprises a second sliding seal disposed between a second portion of the valve and the male fitting.

3. The needleless connector of claim 2, wherein the second sliding seal is configured to maintain separation between the fluid path and the vent path as the second sliding seal slides along an inner surface of the male fitting as the valve moves between the first valve position and the second valve position.

4. The needleless connector of claim 1, wherein the sealing tip and the sliding seal are configured to block the vent path and the fluid path in the first valve position and to open the vent path and the fluid path in the second valve position.

5. The needleless connector of claim 1, wherein the sliding seal is configured to be in sealing contact with the male fitting in the first valve position and not to be in the sealing contact with the male fitting in the second valve position, and wherein the sliding seal seals the vent path closed in the first valve position.

6. The needleless connector of claim 1, wherein the valve comprises a finger disposed within a portion of the sliding seal and external to the portion of the male fitting, and wherein the sliding seal comprises a shoulder proximate to the finger.

7. The needleless connector of claim 6, wherein displacement of the shoulder is configured to move the sliding seal and cause the shoulder to contact the finger and move the valve from the first valve position to the second valve position.

8. The needleless connector of claim 1, wherein the sliding seal comprises a portion fixedly sealed to the body.

9. The needleless connector of claim 1, wherein the valve comprises a lateral fluid passage open to an interior of the male fitting and a longitudinal fluid passage connected to the lateral fluid passage.

10. The needleless connector of claim 9, wherein the fluid path extends through the longitudinal fluid passage and the lateral fluid passage.

11. The needleless connector of claim 10, wherein the body comprises a port, and wherein displacing the valve to the second valve position is configured to open a seal between the lateral fluid passage and the port.

12. The needleless connector of claim 1, wherein the sliding seal is in sealing contact with a recess in the male fitting in the first valve position and the sliding seal is drawn away from the recess in the second valve position.

13. A needleless connector set, comprising:
a male connector comprising:
a first body having a proximal end with a male fitting and an opposing distal end;
a valve disposed within the first body, the first body and the valve defining a vent path between the distal end and the proximal end and a fluid path between the distal end and the proximal end, each of the vent path and the fluid path extending from a most proximal surface of the proximal end to a most distal surface of the distal end;
a sealing tip disposed over a portion of the valve; and
a sliding seal disposed over a portion of the male fitting, wherein the sealing tip and the sliding seal are configured to one of:
open the vent path before opening the fluid path as the valve moves from a first valve position to a second valve position; and
open the fluid path before opening the vent path as the valve moves from the first valve position to the second valve position; and
a female connector comprising:
a second body; and
a collapsible valve disposed within the second body,
wherein the valve of the male connector is in the first valve position when the male connector and the female connector are not mated and in the second valve position when the male connector and the female connector are mated.

14. The needleless connector set of claim 13, wherein the sealing tip and the sliding seal are configured to block the vent path and the fluid path in the first valve position and to open the vent path and the fluid path in the second valve position.

15. The needleless connector set of claim 13, wherein the sliding seal is configured to be in sealing contact with the male fitting in the first valve position and not to be in the sealing contact with the male fitting in the second valve position, and wherein the sliding seal seals the vent path closed in the first valve position and does not seal the vent path in the second valve position.

16. The needleless connector set of claim 15, wherein the valve of the male connector comprises a finger disposed within a portion of the sliding seal and external to the portion of the male fitting, wherein the sliding seal comprises a shoulder proximate to the finger, and wherein displacement of the shoulder is configured to move the sliding seal and cause the shoulder to contact the finger and move the valve of the male connector from the first valve position to the second valve position.

17. The needleless connector set of claim 16, wherein the second body of the female connector is configured to displace the shoulder when the male connector and the female connector are mated.

18. The needleless connector set of claim 13, wherein the sealing tip and the sliding seal are configured to open the vent path and the fluid path at different points between the first valve position and the second valve position.

19. The needleless connector set of claim 13, wherein the sealing tip comprises a second sliding seal disposed between a second portion of the valve and the male fitting, and wherein the second sliding seal is configured to maintain separation between the fluid path and the vent path as the second sliding seal slides along an inner surface of the male fitting as the valve moves between the first valve position and the second valve position.

* * * * *